United States Patent
Suzuki et al.

(10) Patent No.: US 6,759,052 B1
(45) Date of Patent: Jul. 6, 2004

(54) COSMETIC COMPOSITION

(75) Inventors: Kazuhiro Suzuki, Tokyo (JP); Satsuki Miyagawa, Tokyo (JP); Kei Inagawa, Tokyo (JP); Soichiro Watanabe, Tokyo (JP); Noboru Naito, Tokyo (JP)

(73) Assignee: Kosé Corporation, Tokyo (JP)

( * ) Notice: Subject to any disclaimer, the term of this patent is extended or adjusted under 35 U.S.C. 154(b) by 92 days.

(21) Appl. No.: 10/161,734

(22) Filed: Jun. 5, 2002

(51) Int. Cl.[7] .............................. A61K 7/00; A61K 7/50
(52) U.S. Cl. ...................... 424/401; 424/400; 510/130; 514/937; 514/938
(58) Field of Search ................................ 424/400, 401; 510/130, 220, 235, 470, 505, 514; 514/937, 938

(56) References Cited

U.S. PATENT DOCUMENTS 5,877,144 A    3/1999   Ehrhardt et al.
6,066,316 A  * 5/2000   Shiojima et al. ......... 424/70.19

* cited by examiner

Primary Examiner—Shelley A. Dodson
(74) Attorney, Agent, or Firm—Sherman & Shalloway

(57) ABSTRACT

The present invention is a cosmetic composition comprising, component (A) and component (B), wherein, (A) is carboxylic acid ester of inulin and/or hydrolyzed inulin whose degree of substitution by acyl group is larger than 1, and (B) is cyclic silicone oil, and the present invention is the oily cosmetic compound further containing oleophilic component. More over, the present invention is the W/O type emulsified cosmetic composition prepared by further adding aqueous component and an emulsifier to above mentioned cosmetic compound. In the present invention, acyl group composing component (A) is desirable to be an acyl group of carbon number 14 to 22. Further, a part or all of acyl group composing component (A) is desirable to be palmiroyl group and/or stearoyl group. Furthermore, the above mentioned cosmetic composition can contain dextrin carboxylic acid ester whose degree of substitution by acyl group is 1.6 to 2.5. The cyclic silicone oil of component (B) is at least one selected from the group consisting of octamethylcyclotetrasiloxane, decamethylcyclopentasiloxane and dodecamethylcyclohexasiloxane. The cosmetic composition of the present invention has light feel and is excellent in stability and fluidity.

15 Claims, No Drawings

COSMETIC COMPOSITION

BACKGROUND OF THE INVENTION

1. Field of the Invention

The present invention relates to a cosmetic composition having light feel at the actual use and stability. More in detail, the present invention relates to an oily cosmetic composition which has good dispersing ability of powder in a case when powder is contained, light feel at the actual use, and has excellent stability, further has good fluidity in the case of liquid cosmetic composition. Furthermore, the present invention relates to a W/O type emulsified cosmetic composition which has good stability for preservation, good fluidity, good extending and spreading feature at the actual use and has light feel.

2. Description of the Prior Art

An oily composition is the formulation type which is broadly used in cosmetic use or pharmaceutical use, because it has excellent resistance to sweat and to water. Especially, in the case of makeup cosmetic, it is useful as the formation type which has good effect such as long lasting ability of makeup. Up to the present, for the purpose to improve the stability of the oily makeup cosmetic, especially to improve the dispersion stability of pigment (powder), the methods to blend solid oil or semi-solid oil by high concentration or to blend a gelling agent were carried out. Consequently, almost all of oily makeup cosmetics are a solid type. Further, silicone oil is frequently used to a cosmetic composition because of it's light feel and excellent water resistance, and expected to be a base oil of the oily makeup cosmetic compositions.

However, since above mentioned conventional oily makeup cosmetic composition contains solid oil, semi-solid oil or gelling agent to improve the dispersion stability of pigment in components, there are fusing and filling up process and cooling and solidifying process in the preparing process, and the form of product is mainly a solid type such as stick type. Further, since it contains solid oil or semi-solid oil, feeling such as extending or spreading is not so smooth. And, the blending of solid oil, semi-solid oil or gelling agent is effective when oil is hydrocarbon oil, ester oil or glyceride oil, however, when in the case which large quantity of silicone oil is contained, remarkable effect can not be expected.

Further, the W/O type emulsion is a formation type which is broadly used in cosmetic use or pharmaceutical use, because it has excellent resistance to sweat and to water, especially in the field of cosmetic composition it is noticed that it is the formation type which has an excellent effect such as long lasting ability of makeup. For the purpose to improve the stability of the W/O type emulsified cosmetic composition, a lot of countermeasures were took up to the present. For example, a method to provide a thixotropic feature to the outer phase oil, a method to blend solid oil or semi-solid oil to the outer phase oil by high concentration, a method to blend an electrolyte substance to the inner phase water, a method to gel the inner water, a method to raise the ratio of inner water or the method to increase the blending amount of the surface active agent can be mentioned.

Among the above mentioned method to improve the stability of the W/O type emulsified cosmetic composition, the method to provide a thixotropic feature to the outer phase oil is the most popular measure. Concretely, it is the method to blend an oil gelling agent such as organic modified clay mineral, sucrose carboxylic acid ester or dextrin carboxylic acid ester. For example, in JP Laid Open Publication 8-277302, there is a disclosure that the dextrin ester of normal chain fatty acid, branched fatty acid and/or unsaturated fatty acid is effective in providing high thixotropy as a gelling agent.

Silicone oil is broadly used to the cosmetic composition because of it's specific light feel and good water resistance. Especially, cyclic silicone oil such as octamethylcyclotetrasiloxane has light feel and volatile feature, it is expected to be used as an outer phase oil of W/O type emulsified cosmetic composition for the purpose to perform light feel on skin. However, the technique to improve the 'stability of said W/O type emulsified cosmetic composition is effective in the case when the outer phase oil is hydrocarbon oil, ester oil or glyceride oil, while, in the case when the outer phase oil contains high amount of cyclic silicone oil, remarkable effect can not be obtained.

The present invention is carried out concerning above mentioned circumstances, and the object of the present invention is to provide an oily cosmetic composition which is excellent in stability, further is excellent in fluidity in the case of liquid cosmetic composition and good dispersing ability of powder. Further, another object of the present invention is to provide an improved W/O type emulsified cosmetic composition containing higher amount of cyclic silicone oil in the outer phase oil, that is, stability of which is improved maintaining light feel, which is an original feature of cyclic silicone oil, further has an excellent fluidity and good dispersing ability of powder.

BRIEF SUMMARY OF THE INVENTION

The present invention is carried out based on the knowledge that carboxylic acid ester of inulin and/or hydrolyzed inulin whose degree of substitution by acyl group is larger than 1 are suited as the component to enhance the viscosity of cyclic silicone oil, namely as the gelling agent, and by blending these components in combination to cosmetic composition, the stability of the cosmetic composition can be improved.

That is, the present invention is the cosmetic compound containing (A) inulin carboxylic acid ester whose degree of substitution by acyl group is larger than 1 and/or hydrolyzed inulin carboxylic acid ester whose degree of substitution by acyl group is larger than 1 (shortened: carboxylic acid ester of inulin and/or hydrolyzed inulin whose degree of substitution by acyl group is larger than 1) and (B) cyclic silicone oil. Further, the present invention is the oily cosmetic composition, wherein said cosmetic composition further containing an oleophilic component. Furthermore, the present invention is a W/O type emulsified cosmetic composition, wherein said cosmetic composition further containing an aqueous component and an emulsifier.

As the desirable example of carboxylic acid which composes component (A), carboxylic acid of carbon number 14 to 22 can be mentioned. Further, a part or all of carboxylic acid of (A) is desirable to be palmitoyl group and/or stearoyl group. Furthermore, dextrin carboxylic acid ester whose degree of substitution by acyl group is 1.5 to 2.5 can be blended to above mentioned cosmetic composition. As the cyclic silicone oil of component (B), it is desirable to use at least one cyclic silicone oil selected from the group consisting of octamethylcyclotetrasiloxane, decamethylcyclopentasiloxane and dodecamethylcyclohexasiloxane.

Further, the present invention is the oily makeup cosmetic composition containing (A-1) 5–20 wt. % of a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 2.5 to the total weight of (A-1), (B) 30–90 wt. % of at least one cyclic silicone oil selected from the group consisting of octamethylcyclotetrasiloxane, decamethylcyclopentasiloxane and dodecamethylcyclohexasiloxane and (C) 0.1–40 wt. % of powder. Said component (A-1) is desirable to be a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 1.7 to the total weight of (A-1), wherein the blending ratio of (a) and (b) is (b)/(a)= 0.5–2.

Furthermore, the present invention is a W/O type emulsified cosmetic composition containing (A-1) 1–20 wt. % of a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 2.5 to the total weight of (A-1), (B) 10–90 wt. % of at least one cyclic silicone oil selected from the group consisting of octamethylcyclotetrasiloxane, decamethylcyclopentasiloxane and dodecamethylcyclohexasiloxane, (D) 0.1 to 10 wt. % of an emulsifier and (E) 1–80 wt. % of aqueous component. Said component (A-1) is desirable to be a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 1.7 to the total weight of (A-1), wherein the blending weight ratio of (a) and (b) is (b)/(a)=0.5–2. In the present invention, the degree of substitution by acyl group means the average degree of substitution (indicated by mole number of carboxylic acid which was acylated per one monosaccharide unit) of polysaccharide carboxylic acid estrers, for example, carboxylic acid ester of inulin and/or hydrolyzed inulin, dextrin carboxylic acid ester and so on.

DETAILED DESCRIPTION OF THE INVENTION

Regarding to Component (A)

Component (A) used in the present invention is carboxylic acid ester of inulin and/or hydrolyzed inulin whose degree of substitution by acyl group is larger than 1. Said carboxylic acid ester of inulin and/or hydrolyzed inulin whose degree of substitution by acyl group is larger than 1 is excellent by alone in gelling ability of cyclic silicone oil such as octamethylcyclotetrasiloxane, decamethylcyclopentasiloxane and dodecamethylcyclohexasiloxane and can improve the stability maintaining good fluidity of cosmetic composition.

Inulin used in component (A) is a kind of polysaccharide and is oligosaccharide mainly composed of D-fructose. Inulin is composed of β-1,2 bonded chain of franoidfructose unit which has a structural feature possessing a saccharose bonded α-D-glucose at the reducing end group. Inulin can be obtained from a plant belonging to a chrysanthemum family, for example, chicory or dahlia. Inulin which can be used in the present invention is the inulin whose franoidfructose unit is about 3 to 60. Further, hydrolyzed inulin can be also used.

The desirable carboxylic acid to be used in component (A) is the normal chain carboxylic acid of carbon number 14 to 22. And, a part or all of carboxylic acid of (A) is further desirable to be palmitic acid of carbon number 16 and/or stearic acid of carbon number 18. Degree of substitution of carboxylic acid per one fructose unit of inulin in component (A) is larger than 1. If the degree of substitution is less than 1, the solubility of octamethylcyclotetrasiloxane, decamethylcyclopentasiloxane or dodecamethylcyclohexasiloxane to cyclic silicone oil is deteriorated and the preparation of the stabilized cosmetic composition is difficult.

Inulin carboxylic acid ester of component (A) whose degree of substitution by acyl group is larger than 1 can be prepared by reacting said inulin with carboxylic acid or carboxylic acid derivatives. As the carboxylic acid derivatives, acid halide or acid anhydride can be mentioned. The reaction of inulin with carboxylic acid or carboxylic acid derivatives can be easily carried out by well-known method. For example, it can be obtained by the method to disperse inulin in N,N-dimethylformamide or pyridine, then to add carboxylic acid halide or carboxylic acid anhydride and to react at the temperature of approximately 60° C. for about 2 hours.

Above mentioned component (A) can gel the cyclic silicone oil by alone, however, when it is used by combination with dextrin carboxylic acid ester of degree of substitution by acyl group from 1.6 to 2.5, it can further improve the stability of a cosmetic composition maintaining good fluidity of the cosmetic compound.

Regarding to Component (A-1)

Component (A-1) is a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 2.5 to the total weight of (A-1). Said component (a) is same as to the component (A) illustrated above.

The desirable dextrin used in the component (b) is that having average saccharide polymerization degree of 3 to 150. The degree of substitution by acyl group of dextrin per glucose unit is from 1.5 to 2.5, desirably is from 1.5 to 1.7. When the degree of substitution is less than 1.5 or over than 2.5, the soluble temperature of the component (b) becomes high, and it becomes hard to be blended in cosmetic composition. The desirable carboxylic acid to be used in the component (b) is a normal chain fatty acid of carbon number 8 to 22, more desirably is a normal chain fatty acid of carbon number 12 to 20, and especially desirable to be palmitic acid of carbon number 16.

The dextrin carboxylic acid ester whose degree of substitution by acyl group is 1.5 to 2.5 of the component (b) can be prepared by reacting said dextrin and carboxylic acid or carboxylic acid derivatives. As the carboxylic acid derivatives, such as acid halide or acid anhydride can be used. The reaction of dextrin with carboxylic acid or carboxylic acid derivatives can be easily carried out by well-known method. For example, it can be obtained by the method to disperse dextrin into N,N-dimethylformamide or pyridine, then to add carboxylic acid halide or carboxylic acid anhydride and to react at the temperature of approximately 60° C. for about 2 hours. As the product of the component (b) to be used in the present invention and can be purchased from the market, Rheopearl TL and Rheopearl KL (product of Chiba Flour Milling Co., Ltd.) can be mentioned. by weight. In the case of oily makeup cosmetic composition, when said ratio is less than 0.5 fluidity deteriorates, and when is over than 2, gelling of cyclic silicone oil is not sufficient, and the dispersion stability of powder e.g. pigment deteriorates. And in the case of W/O type emulsified cosmetic composition, when said ratio is smaller than 0.5 fluidity deteriorates, and when over than 2, gelling of cyclic silicone oil is not sufficient, and emulsion stability deteriorates.

In this case, a gelling agent of the component (A-1) contains both components (a) and (b) as the necessary component. The gelling agent of the component (A-1) may contain a gelling agent except components (a) and (b), however it is desirable that the total weight of components (b) and (a) is larger than 50 wt. % of the gelling agent of (A-1) at the actual use (hereinafter, "wt. %" is described as just "%"). Desirably, this percentage is larger than 70%. In the case when a gelling agent except components (a) and (b) is used, the kind of it is not restricted. As the concrete example, dextrin carboxylic acid ester possessing a substitution group except components (a) and (b) of the present invention, inulin and/or hydrolyzed inulin carboxylic acid ester, sucrose fatty acid ester, acylamino acid derivatives, metallic soap or organic modified clay mineral can be used.

In an oily cosmetic composition, the blending amount of gelling agent of component (A-1) is from 5 to 20%. When the amount of gelling agent of component (A-1) is smaller than 5%, the preparation of stabilized oily cosmetic composition becomes difficult and when the amount of gelling agent is larger than 20%, the fluidity of the oily cosmetic composition is deteriorated. And, in the case of W/O type emulsified cosmetic composition, the gelling agent of component (A-1) acts as the gelling agent for the outer phase oil. The blending amount of gelling agent of component (A-1) is from 1 to 20%. When the amount of gelling agent is smaller than 1%, the preparation of stabilized W/O type emulsified cosmetic composition becomes difficult. And in the case of liquid W/O type emulsified cosmetic composition, when the amount of gelling agent is larger than 20%, the fluidity of the oily cosmetic composition is deteriorated.

Regarding to Component (B)

The component (B) is cyclic silicone oil. As the cyclic silicone oil, octamethylcyclotetrasiloxane, decamethylcyclopentasiloxane, dodecamethylcyclohexasiloxane or others can be used. These compounds can be used alone or can be used together with.

In oily cosmetic composition, it is desirable to contain 30 to 90% of cyclic silicone oil of component (B). In the case of W/O type emulsified cosmetic composition, it is desirable to contain 10 to 90% of cyclic silicone oil of component (B).

Regarding to Component (C)

To the oily cosmetic composition, powder is blended as the component (C) aiming to perform makeup effect. The blending amount is preferably from 0.1 to 40%. The powder to be blended is not restricted to the shape of it e.g. spherical, plate shape or needle shape, to the particle size of it e.g. fumed size, fine particle size or pigment size or to the structural feature e.g. porous or non porous. And, inorganic powder, brilliant powder, organic powder, pigment powder and complex powder can be mentioned. As the concrete example, following powders can be mentioned. That is, as a coloring agent, titanium dioxide, black titanium oxide, prussian blue, ultramarine, red oxide of iron, yellow oxide of iron, black oxide of iron, zinc oxide, aluminum oxide, magnesium oxide, zirconium oxide, magnesium carbonate, calcium carbonate, barium sulfate, chromium oxide, chromium hydroxide, carbon black or tar pigment; as a feeling adjusting agent, aluminum silicate, magnesium silicate, aluminum magnesium silicate, mica, synthetic mica, synthetic sericite, sericite, talc, silicon carbide, boron nitride, nylon powder, polymethylmethacrylate powder, powder of acrylonitrile-methacrylic acid copolymer, powder of vinyliden chloride-methacrylic acid copolymer, wool powder, silk powder, urethane powder, crystalline cellulose or N-acyllysine; as a brilliant powder, oxychlorobismuth, titanated mica, iron oxide coated mica, iron oxide coated titanated mica, organic pigment coated titanated mica or aluminum powder; as an UV shuttering agent, complex powder such as fine particle of titanium dioxide, fine particle of zinc oxide, fine particle of titanium dioxide coated mica, fine particle of zinc oxide coated titanated mica, fine particle of barium sulfate coated titanated mica can be mentioned. These kinds of powder can be used alone or can be used together with. For the purpose to improve the dispersability or adhesion, these kinds of powder can be surface treated by silicones, fluorine compounds, metallic soaps and oil composition using general well-known method.

Regarding Compound (D)

To the W/O type emulsified cosmetic composition, an emulsifier of component (D) is blended. As the emulsifier to be blended to the cosmetic composition of the present invention, any kind of emulsifier which forms W/O type emulsion can be used, and not restricted. For example, surface active agent such as nonion surface active agent or amphoteric surface active agent, or oil composition which has specific feature to hold water in oil without using surface active agent can be used. These compounds can be used by alone or can be used together with. Especially the use of nonion surface active agent is desirable.

As the concrete example of nonion surface active agent, silicone surface active agent such as polyoxyalkylene modified organopolysiloxane, polyoxyalkylene and alkyl co-modified organopolysiloxane; sorbitane fatty acid ester surface active agent such as sorbitane sesquioleate; glycerin fatty acid surface active agent such as glyceryl stearate; polyglycerin fatty acid surface active agent such as diglycerin diisostearate, diglycerin monoisostearate, decaglycerin dioleate; polyoxyethylene surface active agent such as polyoxyethylenesorbit hexastearate, polyoxyethylenesorbit tetraoleate, polyoxyethylenemonostearate, polyoxyethylene cetylether, polyoxyethylene oleylether, polyoxyethylene caster oil, polyoxyethylenesorbit bees wax can be mentioned. Nonion surface active agent whose HLB value is not exceed 10 (10 is included) is desirably used.

Especially, among nonion surface active agent, the silicone surface active agent such as polyoxyalkylene modified organopolysiloxane represented by general formula (1) and long chain containing polyoxyalkylene modified organopolysiloxane represented by general formula (2) are desirable.

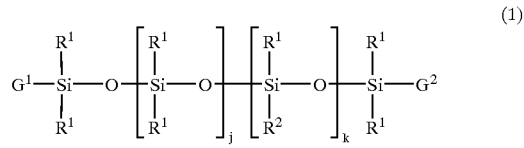

(1)

[in the formula, $R^1$ is an alkyl group of carbon number 1–5 or phenyl group. $R^2$ is $-Q^1-O-(C_2H_4O)_h-(C_3H_6O)_i-R^3$ (wherein $Q^1$ is a divalent hydrocarbon group of carbon number 1–5, $R^3$ is a hydrogen atom, alkyl group of carbon number 1–5 or acetyl group. h is an integer of 1–50, i is an integer of 0–50.) $G^1$ and $G^2$ can be same or can be different and respectively indicates $R^1$ or $R^2$. j is an integer of 0–150 and k is an integer 0–50. And, when k=0, at least one of $G^1$ or $G^2$ is $R^2$].

(2)

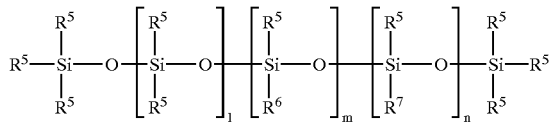

[in the formula, $R^1$ is an alkyl group of carbon number 1–5 or phenyl group. $R^7$ is $-Q^2-O-(C_2H_4O)_c-(C_3H_6O)_d-R^9$, $Q^2$ is a divalent hydrocarbon group of carbon number 1–5, $R^9$ is a hydrogen atom, alkyl group of carbon number 1–5 or acetyl group. c is an integer of 1–50, d is an integer of 0–50. $R^6$ is indicated by $-(C_3H_6O)_e-R^{10}$, and e is an integer of 0–5, $R^{10}$ is an alkyl group of carbon number 6–18. l is an integer of 5–150, m is an integer of 5–40 and n is an integer of 2–40.]

The blending amount of an emulsifier in W/O type emulsified cosmetic composition of the present invention is preferably from 0.1 to 10%. Within this limit, the W/O type emulsified cosmetic composition excellent in light feel, stability and fluidity can be obtained.

Regarding Compound (E)

The component (E) in W/O type emulsified cosmetic composition is an aqueous component. The aqueous component forms a water phase and water is a necessary component, and blended to the W/O type emulsified cosmetic composition as an inner water phase. The aqueous component can contain any kinds of water soluble component except water, for example, alcohol, glycol, saccharide, water soluble polymer, skin care component, preservative and antifungal agent, antioxidation agent or UV ray absorbing agent in the limit not to disturb the effect of the present invention. The blending amount of the aqueous component in the W/O type emulsified cosmetic composition of the present invention is preferably from 1 to 80%.

The oily cosmetic composition of the present invention is characterized to have light feel originated to component (B). Further, since component (A) or (A-1) is contained as a gelling agent component (B) can be gelled maintaining fluidity. And, it is suited to the oily makeup cosmetic composition because it can disperse powder well and can improve the dispersing stability.

In the oily cosmetic composition of the present invention, a dispersing agent can be added besides above mentioned component (A-1), component (B) and component (C). As a dispersing agent which is possible to the cosmetic composition of the present invention, any kinds of agent which disperse powder e.g. pigment necessary for makeup can be used, and is not restricted. As the concrete example, nonion surface active agent ionic surface active agent, amphoteric surface active agent, or oil composition which has specific feature to hold water in oil without using surface active agent can be mentioned. These compounds can be used by alone or can be used together with. As the nonion surface active agent, the nonion surface active agent mentioned in above mentioned component (D) can be used. The blending amount of a dispersing agent in the oily cosmetic composition is the necessary amount to form stable dispersion, and desirably to be 0.1 to 10%. Within this limit, the oily cosmetic composition which is excellent in light feel, stability and fluidity can be obtained.

The cosmetic composition of the present invention may contain an oleophilic component. The oleophilic component except component (B), can be solid state, semi-solid state or liquid state, further, can be animal oil, vegetable oil, mineral oil or synthetic oil. Hydrocarbons, fats, waxes, esters, carboxylic acids, higher alcohols, organopolysiloxanes, fluorocarbon oils or oleophilic surface active agents can be used. For example, liquid paraffin, squalane, polybuten, vaseline, paraffin wax, ceresin wax, microcrystaline wax, olive oil, caster oil, jojoba oil, macadamian nut oil, japan wax, bees wax, candelilla wax, carnauba wax, lanoline, isopropyl myristate, isopropyl palmitate, cetyl-2-ethylhexanoate, octyldodecyl myristate, pentaerythritol rhodinate, glyceryl trioctanoate, diglyceryl triisostearate, stearic acid, lauric acid, oleic acid, behenic acid, cetanol, stearyl alcohol, oleyl alcohol, behenyl alcohol, dimethylpolysiloxane, methylphenylpolysiloxane, methylhydrogenpolysiloxane, dimethylpolysiloxane having three dimensional crosslinking structure, perfluorooctane, perfluorodecane or perfluoropolyether can be mentioned. These compounds can be used alone or can be used together with.

Further, to the oily cosmetic composition of the present invention, an oil soluble resin can be blended besides above mentioned components. As the oil soluble resin which can be blended in the present invention, any kind of compound which meets the object such as improvement of long lasting effect, providing brilliance, providing water resistance or oil resistance or improvement of feeling at the practical use can be used, and is not restricted. For example, vinyl resin, (meth) acrylic acid resin, maleic acid resin, terpenoid resin, cellulose resin or organic silicone resin can be mentioned, and these resins can be used by alone or can be used together with. As the vinyl resin, polyethylene, polypropylene, polybutylene, polyisobuthylene, polyvinylacetate or polyvinylalcoholalkylether can be mentioned. As (meth) acrylic acid resin, polyacrylic acid alkyl, polymethacrylic acid alkyl or polycrotonic acid alkyl can be mentioned. As the terpenoid resin, rhodinic acid ester, modified rhodinic acid ester by hydrogenation, disproportionation or polymerization can be mentioned, and as the organic silicone resin, trimethylsiloxysilicate can be mentioned. The blending amount of the oil soluble resin in the oily cosmetic composition of the present invention is depends on the kind of oil composition or combination and can not be restricted, however, is almost in the range of 0.1 to 10%.

Further, in the W/O type emulsified cosmetic composition of the present invention, since cyclic silicone oil of above mentioned component (B) is existing, it has the light feel originated to said cyclic silicone oil. And, since component (A) or (A-1) is contained, it becomes possible to provide thixotropic feature to the outer phase oil containing component (B), so that the stability of the cosmetic composition is improved and provide good fluidity to the cosmetic composition. Therefore, the W/O type emulsified cosmetic composition of the present invention possessing light feel, excellent stability and good fluidity.

To the W/O type emulsified cosmetic composition of the present invention, powder can be blended in accordance to the object besides above mentioned components (A-1), (B) and (D), in the range not to hurt the effect of the present invention. As the powder, the powder which are mentioned in above mentioned component (C). The blending amount of the powder to the W/O type emulsified cosmetic composition of the present invention is depending on the object and can not be restricted, however, is almost in the range of 0.1 to 40%.

Further, in the W/O type emulsified cosmetic composition of the present invention, an oil soluble resin can be blended besides above mentioned components. As the oil soluble resin which can be blended in the present invention, any kind of compound which meets the object such as providing brilliance, providing water resistance or oil resistance improvement of feeling at the practical use can be used and not restricted, and above mentioned resins can be mentioned. The blending amount of the oil soluble resin in the W/O type emulsified cosmetic composition of the present invention is depends on the kind of oil composition or combination and can not be restricted, however, is almost in the range of 0.1 to 10%.

As the oily makeup cosmetic compound of the present invention, sunscreening composition, foundation, controlling color, concealer, cheek rouge, eye shadow, eye liner, eyebrow color, mascara, lip stick, lip balm, lip over coat, hair coloring composition or body coloring composition can be mentioned. Further, as the W/O type emulsified cosmetic composition of the present invention, milk lotion, cream, beauty lotion, sun screening composition, foundation, controlling color, concealer, cheek rouge, eye shadow, eye liner, eyebrow color, mascara, eye cream, lip stick, lip over coat, body lotion, hair cream or hair conditioner can be mentioned.

EXAMPLES

The present invention will be understood more readily with reference to the Examples and the Comparative Examples.

Synthesis Example of Carboxylic Acid Ester of Inulin or Hydrolyzed Inulin

Synthesis Example 1
Synthesis of Hydrolyzed Inulin Stearate 500 g of N,N-dimethylformamide was added to 10.8 g of hydrolyzed inulin (commercial name is [RAFTILOSE® P95], product of ORAFTI Co., Ltd., saccharide polymerization degree is 2–7), stirred and dissolved at 60° C. Then, 42 g of pyridine was added and 80.7 g of stearoyl chloride was dropped with constant stirring. After 2 hours reaction, pyridine salt was filtrated and N,N-dimethylformamide was evaporated out. Toluene was added to the residue and extracted and dried up using Glauber's salt and solvent was evaporated out. Residue was rinsed by methanol, and then 40 g of hydrolyzed inulin stearate was obtained. The average degree of substitution by acyl group (indicated by mole number of carboxylic acid which is acylated per one monosaccharide unit) of this hydrolyzed inulin stearate was 2.7, which was calculated by deducting the amount of originally existing free carboxylic acid in specimen from the amount of generated carboxylic acid by saponificating definite amount of the specimen.

Synthesis Example 2
Synthesis of Inulin Stearate 500 g of N,N-dimethylformamide was added to 10.8 g of inulin (commercial name is [RAFTILINE® LS], product of ORAFTI Co., Ltd., saccharide polymerization degree is 8–12), stirred and dissolved at 60° C. Then, 42 g of pyridine was added and 80.7 g of stearoyl chloride was dropped with constant stirring. After 2 hours reaction, pyridine salt was filtrated and N,N-dimethylformamide was evaporated out. Toluene was added to the residue and extracted and dried up using Glauber's salt and solvent was evaporated out. Residue was rinsed by methanol, then 45 g of inulin stearate was obtained. The average degree of substitution by acyl group (indicated by mole number of carboxylic acid which is acylated per one monosaccharide unit) of this inulin stearate was 2.6 which was calculated by deducting the amount of originally existing free carboxylic acid in specimen from the amount of generated carboxylic acid by saponificating definite amount of specimen.

Synthesis Example 3
Synthesis of Inulin Palmitate 200 g of N,N-dimethylformamide and 63 g of pyridine was added to 16.2 g of inulin (commercial name is [RAFTILINE® HP], product of ORAFTI Co., Ltd., saccharide polymerization degree is 20–25), stirred and dissolved at 60° C. Then 110 g of palmitoyl chloride was dropped with constant stirring and after 5 hours reaction whole contents were poured into 1L of purified water so as to separate solid phase. This solid phase was filtrated and the residue was rinsed by methanol thus 75 g of inulin palmitate was obtained. The average degree of substitution by acyl group (indicated by mole number of carboxylic acid which was acylated per one monosaccharide unit) of this inulin palmitate was 2.6 which was calculated by deducting the amount of originally existing free carboxylic acid in specimen from the amount of generated carboxylic acid by saponificating definite amount of specimen.

Synthesis Example 4
Synthesis of Hydrolyzed Inulin Palmitate/2-ethyl-hexanoate 50 mL of N,N-dimethylformamide and 51 g of pyridine was added to 16.2 g of hydrolyzed inulin (commercial name is [RAFTILOSE® P95], product of ORAFTI Co., Ltd., saccharide polymerization degree is 2–7), stirred and dissolved at 55° C. Mixture of 60.5 g of pamitoyl chloride and 16.25 g of 2-ethylhexanoyl chloride was dropped to it under nitrogen gas atmosphere with constant stirring and after 3 hours reaction whole contents were poured into 1.5L of purified water so as to separate solid phase. This solid phase was filtrated and the residue was rinsed by methanol, thus 51 g of hydrolyzed inulin palmitate/2-ethylhexanoate was obtained. The average degree of substitution by acyl group indicated by mole number of carboxylic acid which was acylated per one monosaccharide unit) of this hydrolyzed inulin palmitate/2-ethylhexanoate was 2.4 which was calculated by deducting the amount of originally existing free carboxylic acid in specimen from the amount of generated carboxylic acid by saponificating definite amount of specimen.

Synthesis Example 5
Synthesis of Hydrolyzed Inulin Stearate/Isostearate 160 mL of N,N-dimethylformamide and 52 g of pyridine was added to 16.2 g of hydrolyzed inulin (commercial name is [RAFTILOSE® P95], product of ORAFTI Co., Ltd., saccharide polymerization degree is 2–7), stirred and dissolved at 55° C. Mixture of 66.5 g of stearoyl chloride and 33.3 g of isostearoyl chloride was dropped to it under nitrogen gas atmosphere with constant stirring and after 5 hours reaction whole contents were poured into 1.5L of purified water so as to separate solid phase. This solid phase was filtrated and the residue was rinsed by hot water and methanol, thus 65 g of hydrolyzed inulin stearate/isostearate (2:1) was obtained. The average degree of substitution by acyl group (indicated by mole number of carboxylic acid which is acylated per one monosaccharide unit) of this hydrolyzed inulin stearate/isostearate (2:1) was 2.3 which was calculated by deducting the amount of originally existing free carboxylic acid in specimen from the amount of generated carboxylic acid by saponificating definite amount of specimen.

Synthesis Example 6
Synthesis of Inulin Stearate

By same process to Synthesis Example 3 except using 57 g of stearoyl chloride as acyl chloride and 52 g of pyridine, 65 g of inulin stearate was obtained. The average degree of substitution by acyl group (indicated by mole number of carboxylic acid which is acylated per one monosaccharide unit) of this inulin stearate was 1.3 which was calculated by deducting the amount of originally existing free carboxylic acid in specimen from the amount of generated carboxylic acid by saponificating definite amount of specimen.

Synthesis Example 7
Synthesis of Hydrolyzed Inulin 2-ethylhexanoate

By same process to Synthesis Example 5 except using 30 g of 2-ethylhexanoyl chloride as acyl chloride and 200 g of N-methyl-2-pyrrolidinone (instead of N,N-dimethylformamide), 21 g of hydrolyzed inulin 2-ethylhexanoate was obtained. The average degree of substitution by acyl group (indicated by mole number of carboxylic acid which is acylated per one monosaccharide unit) of this hydrolyzed inulin 2-ethylhexanoate was 1.2 which was calculated by deducting the amount of originally existing free carboxylic acid in specimen from the amount of generated carboxylic acid by saponificating definite amount of specimen.

Synthesis Example 8
Synthesis of Inulin Isostearate

By same process to Synthesis Example 3 except using 121 g of isostearoyl chloride as acyl chloride, 82 g of inulin isostearate was obtained. The average degree of substitution by acyl group (indicated by mole number of carboxylic acid which is acylated per one monosaccharide unit) of this inulin isostearate was 2.7 which was calculated by deducting the amount of originally existing free carboxylic acid in specimen from the amount of generated carboxylic acid by saponificating definite amount of specimen.

Synthesis Example 9
Synthesis of Inulin Oleate

By same process to Synthesis Example 3 except using 81 g of oleoyl chloride as acyl chloride and reacting under nitrogen gas atmosphere, 64 g of inulin oleate was obtained. The average degree of substitution by acyl group (indicated by mole number of carboxylic acid which is acylated per one monosaccharide unit) of this inulin oleate was 2.0 which was calculated by deducting the amount of originally existing free carboxylic acid in specimen from the amount of generated carboxylic acid by saponificating definite amount of specimen.

Synthesis Example 10
Comparative Synthesis Example

Synthesis of hydrolyzed inulin stearate (lower degree of substitution)

500 mL of N,N-dimethylformamide and 79.1 of pyridine was added to 81 g of hydrolyzed inulin (commercial name "RAFTILOSE® P95"; product of ORAFTi, saccharide polymerization degree is 2–7), heated to 55° C. and dissolved with constant stirring. Further, continuing constant stirring under nitrogen gas atmosphere, 151 g of stearoyl chloride was dropped and after 5 hours reaction, then the reacted product was poured into 3L of purified water, and solid part was separated. The solid part was filtrated and rinsed by excess methanol and heated so as to dry up. Thus, 98 g of hydrolyzed inulin stearate was obtained. The average degree of substitution by acyl group (indicated by mole number of carboxylic acid which is acylated per one monosaccharide unit) of this hydrolyzed inulin stearate was 0.6 which was calculated by deducting the amount of originally existing free carboxylic acid in specimen from the amount of generated carboxylic acid by saponificating definite amount of specimen.

Synthesis Example 11
Synthesis of Stearic Acid Ester of Origosaccharide Originated of OPHIOPOGONIS TUBER (Hereinafter Shortened to Bakumondou Stearate)

500 g of N,N-dimethylformamide was added to 10.8 g of essence powder of Bakumondou stearate and dissolved at the temperature of 60° C. with constant stirring. 42 g of pyridine was added to, and 80.7 g of stearoyl chloride was dropped to it, and after 2 hours reaction, pyridine salt was filtrated and N,N-dimethylformamide was evaporated out. Toluene was added to the residue so as to extract, and dried up by using Glauber's salt then solvent was evaporated out. The residue was rinsed by methanol, thus 42 g of Bakumondou stearate was obtained. The average degree of substitution by acyl group (indicated by mole number of carboxylic acid which is acylated per one monosaccharide unit) of this Bakumondou stearate was 2.7 which was calculated by deducting the amount of originally existing free carboxylic acid in specimen from the amount of generated carboxylic acid by saponificating definite amount of specimen.

Examples 1–10 and Comparative Examples 1–4
Lip Color Paste

Lip color paste of composition indicated in Table 1 were prepared according following method, and evaluated by items of "light feel", "stability"and "long lasting". The evaluation method for each item are mentioned below. Evaluation results are also summarized in Table 1.

TABLE 1

| | | Example | | | | | | | | | | Comp. Ex. | | | | (%) |
|---|---|---|---|---|---|---|---|---|---|---|---|---|---|---|---|---|
| No. | Content | 1 | 2 | 3 | 4 | 5 | 6 | 7 | 8 | 9 | 10 | 1 | 2 | 3 | 4 |
| 1 | Decametylcyclopentasiloxane | 42 | 46 | 50 | 30 | 85 | 42 | 40 | 40 | 40 | 40 | 42 | 42 | 42 | — |
| 2 | Neopentylglycol di-2-ethylhexanoate | 20 | 20 | 25 | 20 | — | 20 | 20 | 20 | 20 | 20 | 20 | 20 | 20 | 62 |
| 3 | Propyleneglycol dicaprate | 21.1 | 14.1 | 3.6 | 29.6 | 1.6 | 19.1 | 10.5 | 19.5 | 21.5 | 20.5 | 21.1 | 21.1 | 21.1 | 30.1 |
| 4 | Dextrin palmitate (*1) | 4.5 | 4.5 | 4.5 | 5 | 5 | 2 | 6 | 2 | 3 | 6 | 9 | 4.5 | 4.5 | — |
| 5 | Dextrin palmitate (*2) | — | — | — | — | — | — | — | 2 | — | — | — | — | — | — |
| 6 | Inulin carboxylic acid ester (Synt. Ex. 1) | — | 2 | 2 | — | — | — | 3 | 3 | — | — | — | — | — | — |

TABLE 1-continued

| | | Example | | | | | | | | | | Comp. Ex. | | | | (%) |
|---|---|---|---|---|---|---|---|---|---|---|---|---|---|---|---|---|
| No. | Content | 1 | 2 | 3 | 4 | 5 | 6 | 7 | 8 | 9 | 10 | 1 | 2 | 3 | 4 | |
| 7 | Inulin carboxylic acid ester (Synt. Ex. 3) | 4.5 | 2 | — | 5 | 5 | — | — | — | — | 4 | — | — | — | — | |
| 8 | Inulin carboxylic acid ester (Synt. Ex. 4) | — | — | 2 | — | — | 9 | 9 | — | 6 | 5 | — | — | — | — | |
| 9 | Inulin carboxylic acid ester (Synt. Ex. 10) | — | — | 1 | — | — | — | — | 1 | — | — | — | 4.5 | — | — | |
| 10 | Bakumondou stearate (Synt. Ex. 11) | — | — | — | — | — | — | — | — | — | — | — | — | 4.5 | — | |
| 11 | Benzyldimethylstearyl ammonium hectolite | — | 0.5 | — | — | — | — | — | — | 0.5 | 0.5 | — | — | — | — | |
| 12 | Trimethylsiloxysilicate/decamethylcyclopentasiloxane (*3) | 6 | — | 5 | 5 | — | 6 | 10 | 10 | 2 | 2 | 6 | 6 | 6 | 6 | |
| 13 | Polyisobutylene | — | 10 | 5 | — | — | — | 1 | 5 | 0.5 | — | — | — | — | — | |
| 14 | Cetyl dimethicone copolyol (*4) | 1.5 | 0.5 | 1.5 | 5 | 3 | 1.5 | 1 | 1 | 1.5 | 1 | 1.5 | 1.5 | 1.5 | 1.5 | |
| 15 | Perfume | 0.1 | 0.1 | 0.1 | 0.1 | 0.1 | 0.1 | 0.2 | 0.2 | 0.2 | 0.2 | 0.1 | 0.1 | 0.1 | 0.1 | |
| 16 | D & C Red No. 7 | 0.2 | 0.2 | 0.2 | 0.2 | 0.2 | 0.2 | 0.2 | 0.2 | 0.2 | 0.2 | 0.2 | 0.2 | 0.2 | 0.2 | |
| 17 | Preservative | 0.1 | 0.1 | 0.1 | 0.1 | 0.1 | 0.1 | 0.1 | 0.1 | 0.1 | 0.1 | 0.1 | 0.1 | 0.1 | 0.1 | |
| total | | 100 | 100 | 100 | 100 | 100 | 100 | 100 | 100 | 100 | 100 | 100 | 100 | 100 | 100 | |
| Evaluation items | | | | | | | | | | | | | | | | |
| Light feel at actual use | | ⊚ | ⊚ | ⊚ | ○ | ⊚ | ○ | ⊚ | ⊚ | ⊚ | ⊚ | Δ | Δ | ○ | X | |
| Stability | | ⊚ | ⊚ | ○ | ⊚ | ○ | ○ | ⊚ | ○ | ⊚ | ⊚ | X | X | Δ | X | |
| Long lasting | | ⊚ | ○ | ⊚ | ⊚ | ○ | ⊚ | ⊚ | ⊚ | ○ | ○ | ○ | Δ | Δ | X | |

In Table 1

(*1) degree of substitution by acyl group 1.6: Rheopearl TL (product of Chiba Flour Milling)
(*2) degree of substitution by acyl group 2.2: Rheopearl KL (product of Chiba Flour Milling)
(*3) KF7312J (product of Shin-Etsu Chemical)
(*4) KF6015 (product of Shin-Etsu Chemical)

(Preparation Method)

A. Part of components 2 and 3, components 13 and 15 were mixed together homogeneously.
B. Component 1, remaining part of components 2, 3 and components 4–12 were heated, dissolved and mixed homogeneously.
C. A, B and components 14 and 16 were mixed homogeneously.
D. C was contained into a container (capacity: 30 mL, diameter: 5 mm) with rouge brush, and a lip color paste was obtained.

(Evaluation)

(1) Light Feel at the Actual Use

The lip color paste of Examples and Comparative Examples were test used by 30 women panellers, and "light feel" of at the actual use were evaluated by the panellers according to the following judge standard.

<Judge standard>

| [Numbers of paneller whose evaluation is light] | [judgement] |
|---|---|
| 24 or more | ⊚ |
| 23–18 | ○ |
| 17–12 | Δ |
| 11 or less | X |

(2) Stability

The lip color paste of Examples and Comparative Examples were preserved for 3 months under 40° C. condition. The viscosity change was observed, and evaluated by following judge standard.

<Judge standard>

| [Vicosity change] | [judgement] |
|---|---|
| not changed completely | ⊚ |
| not changed almost | ○ |
| slightly changed | Δ |
| obviously changed | X |

(3) Long Lasting

The Lip Color Paste of Examples and Comparative Examples is test used by 30 women panelists, and "Lasting" effect of each samples at the actual use (3 hours) are evaluated by panelists according to the following judge standard.

(Judge standard)

| [Lasting] | [Judgment] |
|---|---|
| very good | ⊚ |
| good | ○ |
| normal | Δ |
| bad | X |

As clearly understood from the results of Table 1, the Lip Color Paste of Examples 1–10 of the present invention are superior to the Lip Color Paste of the Comparative Examples in light feel at the actual use and stability and lasting.

Example 11

Liquid Lipgloss

| (Components) | (%) |
|---|---|
| 1. Decamethylcyclopentasiloxane | 30.8 |
| 2. Octamethylcyclotetrasiloxane | 30.0 |
| 3. Heavy liquid isoparaffin | 6.0 |

-continued

| (Components) | (%) |
|---|---|
| 4. Polybuten (Polybuten 300R; product of Idemitsu Petroleum Chemical) | 8.0 |
| 5. Polybuten (Polybuten 2000H; product of Idemitsu Petroleum Chemical) | 6.0 |
| 6. Polyglyceryltriisostearate | 2.0 |
| 7. Dextrin palmitate (Rheopearl TL; product of Chiba Flour Milling) | 4.0 |
| 8. Hydrolyzed inulin carboxylic acid ester (Synthesis Ex. 5) | 8.0 |
| 9. Carmine coated titanated mica | 4.0 |
| 10. Titanium dioxide coated glass flake | 4.0 |
| 11. D & C Red No. 7 | 0.2 |

(Method for Preparations)
A. Components 1–8 were heated and dissolved, and mixed homogeneously.
B. Component 11 is added to A and mixed homogeneously by a roll mill.
C. Components 9 and 10 were added to B and mixed homogeneously.
D. C was defoamed, contained into a container with brush and liquid lipgloss was obtained.

The obtained liquid lipgloss had light feel and good adhesion at actual use, further is excellent in stability. And the fluidity was not spoiled after long term preservation.

Example 12

Liquid Eye Shadow

| (Components) | (%) |
|---|---|
| 1. Cetyl isooctanoate | 4.0 |
| 2. Isononyl isononanoate | 3.0 |
| 3. Glyceryl triisooctanoate | 4.0 |
| 4. Dipentaerythritol fatty acid ester (COSMOL168 AR; product of Nisshin Oil Mills) | 1.5 |
| 5. Choresteryl hydroxystearate | 1.0 |
| 6. Acylamino acid choresteryl (ELDEW ® CL-20; product of Ajinomoto) | 0.8 |
| 7. Hydroxy stearic acid octyl (Crodamol OHS; product of Croda) | 0.8 |
| 8. Perfluoropolyether (Fomblin HC/04; product of Ausimont) | 0.001 |
| 9. Dextrin palmitate (Rheopearl TL; product of Chiba Flour Milling) | 1.5 |
| 10. Inulin carboxylic acid ester (Synthesis Ex. 3) | 1.5 |
| 11. Inulin carboxylic acid ester (Synthesis Ex. 6) | 0.5 |
| 12. Sucrose fatty acid ester (Sugar Wax S-10E; product of Dai-ichi Kogyo Seiyaku) | 0.7 |
| 13. PPG-4-Cetheth-20 | 0.5 |
| 14. Diglyceryl diisostearate | 0.5 |
| 15. PEG-10 Dimethicone (KF6017; product of Shin-Etsu Chemical) | 2.0 |
| 16. Titanated mica | 5.0 |
| 17. Iron oxide coated titanated mica | 5.0 |
| 18. D & C Red No. 30 | 0.1 |
| 19. D & C Red No. 7 | 0.1 |
| 20. Spherical urethane powder | 12.0 |
| 21. Needle shape light calcium carbonate | 1.0 |
| 22. Talc | 6.0 |
| 23. Decamethylcyclopentasiloxane | 23.499 |
| 24. Octamethylcyclotetrasiloxane | 25.0 |

(Method for Preparation)
A. Components 1–22 were heated and mixed homogeneously.
B. Components 23 and 24 were added to A and mixed homogeneously.
C. B was deformed and filled up in a compact container, thus the liquid eye shadow was obtained.

The obtained liquid eye-shadow had light feel and good adhesion at actual use, further was excellent in stability. And the fluidity was not spoiled after long term preservation.

Example 13

Lipstick

| (Components) | (%) |
|---|---|
| 1. Polyethylene wax | 15.0 |
| 2. Microcrystalline wax | 3.0 |
| 3. Candelilla wax | 2.0 |
| 4. Pentaerythritol rhodinate | 3.0 |
| 5. Inulin carboxylic acid ester (Synthesis Example 2) | 2.0 |
| 6. Propyleneglycol dicaprate | 20.0 |
| 7. Glyceryl trioctanoate | balance |
| 8. Cetyl 2-ethylhexanoate | 10.0 |
| 9. Decamethylcyclopentasiloxane | 5.0 |
| 10. D & C Red No. 6 | 2.0 |
| 11. D & C Red No. 7 | 1.0 |
| 12. FD & C Yellow No. 5 aluminum lake | 2.0 |
| 13. Perfume | q.s. |

(Method for Preparation)
A. Components 1–8 were heated and dissolved homogeneously
B. Components 9–13 were added to A and mixed homogeneously by a roll mill.
C. B was heated, dissolved and filled up in a lipstick container and cooled down, and a lipstick was obtained.

The obtained lipstick had light feel and good adhesion at actual use, further was excellent in stability and long lasting of makeup.

Example 14

Oily Solid Foundation

| (Components) | (%) |
|---|---|
| 1. Carnauba wax | 2.0 |
| 2. Polyethylene wax | 4.0 |
| 3. Liquid paraffine | 10.0 |
| 4. Vaseline | 7.0 |
| 5. Cetyl 2-ethylhexanoate | 10.0 |
| 6. Decamethylcyclopentasiloxane | 15.0 |
| 7. Dimethylpolysiloxane (20 cs) | 5.0 |
| 8. Hydrolyzed inulin carboxylic ester (Synthesis Ex. 1) | 5.0 |
| 9. Titanium dioxide | 10.0 |
| 10. Mica | balance |
| 11. Fine particle of titanium dioxide | 5.0 |
| 12. Red oxide of iron | 0.8 |
| 13. Yellow oxide of iron | 2.5 |
| 14. Black oxide of iron | 0.2 |
| 15. Talc | 10.0 |
| 16. Spherical nylon powder | 2.0 |
| 17. Perfume | q.s. |

(Method for Preparation)
A. Components 1–8 were heated and fused homogeneously.
B. Components 9–17 were added to A and fused homogeneously using a roll mill.
C. B was heated and fused, then plugged into a dish at the temperature of 80° C. and cooled down. Thus the oily solid foundation can be obtained.

The obtained oily solid foundation had light feel and good adhesion at actual use, further was not sticky and was excellent in long lasting of makeup and stability.

Example 15
Eye Shadow

|  | (Components) | (%) |
|---|---|---|
| 1. | Mica | 20.0 |
| 2. | Synthetic mica | balance |
| 3. | Talc | 11.0 |
| 4. | Titanated mica | 4.0 |
| 5. | Iron oxide coated titanated mica | 1.0 |
| 6. | Spherical nylon powder | 3.0 |
| 7. | Methylparaben | q.s. |
| 8. | Inulin carboxylic acid ester (Synthetic Ex. 2) | 1.0 |
| 9. | Inulin carboxylic acid ester (Synthetic Ex. 7) | 1.0 |
| 10. | Dodecamethylcyclohexasiloxane | 8.0 |
| 11. | Dimethylpolysiloxane (6 cs) | 1.0 |
| 12. | Partially cross linked dimethylpolysiloxane (KSG16; product of Shin-Etsu Chemical) | 2.0 |
| 13. | Periluoropolyether (Fomblin HC/04; product of Ausimont) | 2.0 |

(Method for Preparation)
A. Components 1–7 were mixed together.
B. Component 8–12 were heated and mixed homogeneously.
C. B was added to A and mixed homogeneously.
D. Component 13 was added to C and mixed homogeneously.
E. D was pulverized and molded by pressing in an airtight jar bottle (wide), and the eye shadow was obtained.

The obtained eye shadow had light feel and good adhesion in long lasting of makeup and stability.

Example 16
Gel Type Antiperspirant Composition

|  | (Components) | (%) |
|---|---|---|
| 1. | Decamethylcyclopentasiloxane | 50.0 |
| 2. | Aluminum chlorohydrate (Chlorohydol; product of Rheis, Inc) | 25.0 |
| 3. | Hydrolyzed inulin carboxylic acid ester (Synthesis Ex. 1) | 15.0 |
| 4. | Isopropyl myristate | 10.0 |

(Method for Preparation)

All of components were mixed and dispersed at room temperature and heated to 70° C. with stirring.

This mixture then was cast into a mold with stirring slowly, and allowed to cool to room temperature.

Example 17
Gel Type Antiperspirant Composition

|  | (Components) | (%) |
|---|---|---|
| 1. | Decamethylcyclopentasiloxane | 50.0 |
| 2. | Aluminum chlorohydrate (Chlorohydol; product of Rheis, Inc) | 30.0 |
| 3. | Hydrolyzed inulin carboxylic acid ester (Synthesis Ex. 1) | 8.0 |
| 4. | Isotridecyl isononanoate | 5.0 |
| 5. | Polyglycerin carboxylic acid ester (TAISET; product of Taiyo Chemicals) | 5.0 |
| 6. | Behenyl alcohol | 2.0 |

(Method for Preparation)

All of components were mixed and dispersed at room temperature and heated to 70° C. with stirring.

This mixture then was cast into a mold with stirring slowly, and allowed to cool to room temperature.

Example 18
Gel Type Antiperspirant Composition

|  | (Components) | (%) |
|---|---|---|
| 1. | Decamethylcyclopentasiloxane | 55.0 |
| 2. | Aluminum zirconium tetrachloro hydlex GLY (Reach AZP-908SUF; product of Rheis, Inc) | 25.0 |
| 3. | Behenyl alcohol | 10.0 |
| 4. | Isopropyl myristate | 8.0 |
| 5. | Hydrolyzed inulin carboxylic acid ester (Synthesis Ex. 4) | 1.0 |
| 6. | Dextrin palmitate (Rheopearl KL; product of Chiba Flour Milling) | 1.0 |

(Method for Preparation)

All of components were mixed and dispersed at room temperature and heated to 70° C. with stirring.

This mixture then was cast into a mold with stirring slowly, and allowed to cool to room temperature.

Example 19
Aerosol Type Antiperspirant Composition

|  | (Components) | (%) |
|---|---|---|
| 1. | Mixture of n-butane and isobutane | 58.0 |
| 2. | Decamethylcyclopentasiloxane | 30.0 |
| 3. | Aluminum chlorohydrate (Chlorohydol; product of Rheis, Inc) | 10.0 |
| 4. | Hydrolyzed inulin carboxylic acid ester (Synthesis Ex. 1) | 1.0 |
| 5. | Dextrin palmitate (Rheopearl KL; product of Chiba Flour Milling) | 1.0 |

(Method for Preparation)

Components from 2 to 5 were mixed and dispersed at room temperature and heated to 82° C. with stirring and then allowed to cool to 35° C.

Component 2 was added to the resulting mixture written above with stirring and then was entered into a spraying can.

(Estimation of Example 16–19)

The compositions of Examples 16–18 were white gel with a stability of at least one month at 30° C. and at 5° C. The compositions of Examples 16–18 could deliver the antiperspirant compound to the skin without tacky feel and white residue on the skin or clothing effectively.

About the composition of Examples 19, slight white residue vanished within 10 minutes after application to the skin.

Examples 20–29, Comparative Example 5–7
Milky Lotion

Milky lotions composed of components shown in Table 2 were prepared by following method and the obtained milky lotions were evaluated according to the evaluation items of "light feel at the actual use", "stability" and "fluidity" by following evaluation method. The evaluation results were also summarized in Table 2.

TABLE 2

|  | contents | Example 20 | 21 | 22 | 23 | 24 | 25 | 26 | 27 | 28 | 29 | Comparative Example 5 | 6 | 7 (%) |
|---|---|---|---|---|---|---|---|---|---|---|---|---|---|---|
| 1 | Decametylcyclopentasiloxane | 25 | 25 | 30 | 20 | 90 | 30 | 30 | 30 | 30 | 30 | 25 | 25 | — |
| 2 | Neopentylglycol di-2-ethylhexanoate | 10 | 10 | 10 | 10 | — | 10 | 10 | 10 | 10 | 10 | 10 | 10 | 25 |
| 3 | Propyleneglycol dicaprate | 10 | 10 | 5 | 10 | — | 10 | 10 | 10 | 10 | 10 | 10 | 10 | 20 |
| 4 | Dextrin palmitate (*1) | 2 | 2 | 2 | — | 2 | 1 | 8 | 1 | 1.5 | 3 | 4 | 2 | 2 |
| 5 | Dextrin palmitate (*2) |  |  |  |  |  |  |  | 1 |  |  |  |  |  |
| 6 | Hydrolyzed inulin caboxylic acid (synthesis Ex. 1) |  | 1 | 1 |  |  |  |  | 1.5 |  |  |  |  |  |
| 7 | Inulin carboxylic acid (synthesis Ex. 3) | 2 | 1 |  | 4 | 2 | 0.5 |  |  | 3 | 1.5 |  |  | 2 |
| 8 | Hydrolyzed inulin carboxylic acid (synthesis Ex. 4) |  |  | 1 |  |  |  | 12 |  |  |  |  |  |  |
| 9 | Inulin carboxylic acid (synthesis Ex. 10) |  |  | 0.5 |  |  |  |  | 0.5 |  |  |  |  |  |
| 10 | Benzyldimethyl stearyl ammonium hectolite |  | 0.1 |  |  |  |  |  |  |  |  |  |  |  |
| 11 | PEG10 Dimethicone (*3) | 2 | 1.5 | 2 | 2 | 1.5 | 0.5 | 1.5 | 1.5 | 1.5 | 1.5 | 2 | 2 | 2 |
| 12 | Cethyl dimethicone copolyol (*4) |  | 1 |  |  |  | 0.5 |  |  |  |  |  |  |  |
| 13 | Sorbitan sesquioleate | 1 | 0.5 | 0.5 | 1 | 0.5 | 0.5 | 0.5 | 0.5 | 0.5 | 0.5 | 1 | 1 | 1 |
| 14 | Perfume | 0.1 | 0.1 | 0.1 | 0.1 | 0.1 | 0.1 | 0.1 | 0.1 | 0.1 | 0.1 | 0.1 | 0.1 | 0.1 |
| 15 | Purified water | ba. | ba. | ba. | ba. | ba. | ba. | ba. | ba. | ba. | ba. | ba. | ba. | ba. |
| 16 | 1,3-butylene glycol | 10 | 10 | 10 | 10 | — | 10 | 10 | 10 | 10 | 10 | 10 | 10 | 10 |
| 17 | Preservative | 0.5 | 0.5 | 0.5 | 0.5 | 0.5 | 0.5 | 0.5 | 0.5 | 0.5 | 0.5 | 0.5 | 0.5 | 0.5 |
| total |  | 100 | 100 | 100 | 100 | 100 | 100 | 100 | 100 | 100 | 100 | 100 | 100 | 100 |
| Evaluation items |  |  |  |  |  |  |  |  |  |  |  |  |  |  |
| Light feel at actual use |  | ◎ | ◎ | ◎ | ○ | ◎ | ◎ | ◎ | ◎ | ◎ | ◎ | Δ | Δ | X |
| Stability |  | ◎ | ◎ | ◎ | ◎ | ◎ | ○ | ◎ | ○ | ◎ | ◎ | X | X | X |
| Fluidity |  | ◎ | ◎ | ◎ | ○ | ◎ | ◎ | ○ | ◎ | ◎ | ○ | X | X | X |

Remarks: ba. is abbreviation of balance
(*1) degree of substitution by acyl group 1.6: Rheopearl TL (product of Chiba Flour Milling)
(*2) degree of substitution by acyl group 2.2: Rheopearl KL (product of Chiba Flour Milling)
(*3) KF6017 (product of Shin-Etsu Chemical)
(*4) ABIL EM-90 (product of Goldschmidt)

(Method for Preparation)
A. Component 1–13 were heated and mixed homogeneously, then cooled down to the room temperature and component 14 was added.
B. Components 15–17 were mixed homogeneously.
C. A was stirred constantly and B was added slowly to A and emulsifyed.
D. After C was filled into a container (capacity: 95 mL, diameter: 10 mm) and a Milky lotion was obtained.

(Method for Evaluation)
(1) Light Feel at the Actual Use
Same method to Examples 1–10 was used.
(2) Stability
Specimen of Examples and Comparative Examples were preserved in the condition of 40° C. for 3 months. Then the condition of the Milky lotion was observed and evaluated by following judge standard.
<Judge standard>

| [Condition] | [judgement] |
|---|---|
| not changed completely | ◎ |
| not changed almost | ○ |
| slightly changed | Δ |
| obviously changed | X |

(3) Fluidity
Same method to Examples 1–10 was used.
As clearly understood from the results of Table 2, the lotions of Example 20–29 of the present invention were the excellent Milk lotions which were superior to the Milk lotions of Comparative Examples in all evaluation items, namely, "light feel at the actual use", "stability" and "fluidity".

Example 30
Sunscreening Milky Lotion

| (Components) |  |
|---|---|
| 1. Decamethylcyclopentasiloxane | 15.0 |
| 2. Octamethylcyclotetrasiloxane | 15.0 |
| 3. Glyceryl triisooctanoate | 7.6 |
| 4. Trimethylsiloxysilicate/decamethylcyclopentasiloxane (X-21-5250; product of Shin-Etsu Chemical) | 0.25 |
| 5. Trimethylsiloxysilicate/decamethylcyclopentasiloxane (KF9021; product of Shin-Etsu Chemical) | 0.25 |
| 6. C14–15 Dialkyl carbonate (Lialcarb SR-1000/R; product of Enichen) | 5.0 |
| 7. Octyl paramethoxycinnamate | 2.0 |
| 8. Dispersion of fine titanium dioxide particles (Cosmeserve WP-50; product of Dainihon Kasei) | 5.0 |
| 9. Dextrin palmitate (Rheopearl TL; product of Chiba Flour Milling) | 2.5 |
| 10. Hydrolyzed inulin carboxylic acid ester (Synthesis Ex. 5) | 2.5 |
| 11. Silicone treated PMMA spherical bead (SA PMMA MBP-8; product of Miyoshi Kasei) | 2.0 |
| 12. Cetyl Dimethicone copolyol (ABIL EM-90; product of Goldschmidt) | 1.5 |
| 13. PEG-10 Dimethicone (KF6017; product of Shin-Etsu Chemical) | 1.5 |

-continued

| | (Components) | |
|---|---|---|
| 14. | Na.Mg.Li silicate (Laponite ® XLS; product of Laporte) | 0.5 |
| 15. | Ethanol | 5.0 |
| 16. | POE (10E.O.) methylglucoside | 1.0 |
| 17. | Methylparaben | 0.1 |
| 18. | Purified water | 33.4 |

(Method for Preparation)

A. Components 1–10, 12 and 13 were heated and mixed homogeneously.

B. Component 11 was added to A and mixed homogeneously.

C. Components 14–18 were mixed homogeneously.

D. B was stirred constantly and C was added slowly to B and emulsified. Then filled into a container and sunscreening milky lotion.

The obtained sunscreening milky lotion had light feel at actual use and also emulsion condition was good. And the milky lotion showed good fluidity after long term (3 months) preservation.

Example 31

Liquid Foundation

| | (Componens) | (%) |
|---|---|---|
| 1. | Glyceryl tribehenate | 0.5 |
| 2. | Hydrogenated caster oil stearate | 0.5 |
| 3. | Hydrogenated caster oil | 0.5 |
| 4. | Octyl paradimethylaminobenzoate | 3.5 |
| 5. | Neopentylglycol dioctanoate | 6.5 |
| 6. | Dextrin palmitate (Rheopearl TL; product of Chiba Flour Milling) | 2.5 |
| 7. | Hydrolyzed inulin carboxylic acid ester (Synthesis Ex. 5) | 0.6 |
| 8. | Cetyl dimethicone copolyol (ABIL EM-90; product of Goldschmidt) | 3.0 |
| 9. | Polyglycerin carboxylic acid ester | 1.0 |
| 10. | Sorbitan sesquioleate | 1.0 |
| 11. | Sorbitan polyoxyethylenemonooleate | 0.1 |
| 12. | Dimethyl distearyl ammonium hectolite | 0.2 |
| 13. | Benzyl dimethyl stearyl ammonium hectolite | 0.8 |
| 14. | Titanium dioxide | 10.0 |
| 15. | Red oxide of iron | 0.15 |
| 16. | Yellow oxide of iron | 2.0 |
| 17. | Umber | 0.5 |
| 18. | Black oxide of iron | 0.1 |
| 19. | Talc | 3.5 |
| 20. | Propyleneglycol dicaprate | 7.0 |
| 21. | Decamethylcyclopentasiloxane | 12.0 |
| 22. | Octamethylcyclotetrasiloxane | 8.0 |
| 23. | Preservative | 0.1 |
| 24. | Pluronic type surfactant (Unilube 75DE-2620R; product of Nippon Oil & Fats) | 0.2 |
| 25. | Ethanol | 7.5 |
| 26. | Purified water | 30.1 |
| 27. | Perfume | 0.05 |

(Method for Preparation)

A. Components 1–11 were heated and mixed homogeneously.

B. Components 12–19 were added to A and mixed homogeneously using a roll mill.

C. Components 20–22 were added to B and mixed homogeneously.

D. Components 23–26 were mixed homogeneously.

E. D was added to C slowly and emulsified.

F. Component 27 was added to E, mixed together, thus a liquid foundation was obtained.

The liquid foundation had very light feel without tacky feel at the actual use, and also was excellent in stability and fluidity.

Example 32

Liquid Eye Shadow

| | (Components) | (%) |
|---|---|---|
| 1. | Cetyl isostearate | 4.0 |
| 2. | Isononyl isononoate | 2.5 |
| 3. | Glyceryl triisooctanoate | 4.0 |
| 4. | Dipentaerythritol fatty acid ester (COSMOL168 AR; product of Nisshin Oil Mills) | 1.5 |
| 5. | Cholesteryl hydroxystearate | 4.5 |
| 6. | Acylamino acid cholesteryl (ELDEW ® CL-301; product of Ajinomoto) | 0.5 |
| 7. | Octyl hydroxystearate | 0.5 |
| 8. | Perfluoropolyether (Fomblin HC/04; product of Ausimont) | 0.002 |
| 9. | Dextrin palmitate (Rheopearl TL; product of Chiba Flour Milling) | 1.2 |
| 10. | Inulin carboxylic acid ester (Synthesis Ex. 3) | 1.2 |
| 11. | Sucrose carboxylic acid ester (Sugar Wax S-10E; product of Dai-ichi Kogyo Seiyaku) | 0.5 |
| 12. | POE-POP cetylether | 1.0 |
| 13. | Diglyceryl diisostearate | 1.0 |
| 14. | PEG- 10 Dimethicone (KF6017; product of Shin-Etsu Chemical) | 3.0 |
| 15. | Titanated mica | 3.0 |
| 16. | Iron oxide coated titanated mica | 3.0 |
| 17. | Ultramarines | 3.0 |
| 18. | Spherical urethane powder | 3.0 |
| 19. | Dodecamethylcyclohexasiloxane | 15.0 |
| 20. | Octamethylcyclotetrasiloxane | 15.0 |
| 21. | Glycerin | 0.5 |
| 22. | Propylene glycol | 3.0 |
| 23. | Ethanol | 3.0 |
| 24. | Magnesium aluminum silicate | 0.05 |
| 25. | EDTA-2Na | 0.1 |
| 26. | Hydroxymethoxybenzophenon sulfanate | 0.05 |
| 27. | Preservative | 0.1 |
| 28. | Purified water | balance |

(Method for Preparation)

A. Components 1–14 were heated, dissolved and mixed homogeneously.

B. Components 15–18 were added to A and mixed homogeneously, then components 19, 20 were added and mixed homogeneously.

C. Components 21–28 were mixed homogeneously.

D. C was added to B slowly and emulsified, then poured into a container.

Thus the liquid eye shadow was obtained.

The obtained eye shadow had light feel and good adhesion at the actual use, and also excellent in stability and fluidity.

Example 33

Hair Set Lotion

| | (Components) | (%) |
|---|---|---|
| 1. | Decamethylcyclopentasiloxane | 40.0 |
| 2. | Octamethylcyclotetrasiloxane | 30.0 |
| 3. | Olive oil | 0.2 |
| 4. | Phenyl Trimethicone | 0.4 |
| 5. | Liquid lanolin | 0.5 |
| 6. | Dilute product of highly polymerized methyl polysiloxane/decamethylcyclopentasiloxane (BY11-003; product of Dow Corning) | 0.4 |

-continued

| | (Components) | (%) |
|---|---|---|
| 7. | Trimethylsiloxysilicate/decamethylcyclopentasiloxane (KF7312J; product of Shin-Etsu Chemical) | 0.2 |
| 8. | Dextrin palmitate (Rheopearl TL; product of Chiba Flour Milling) | 0.5 |
| 9. | Hydrolyzed inulin carboxylic acid ester (Synthesis Ex. 4) | 2.5 |
| 10. | PEG-3 Dimethicone (KF6015; product of Shin-Etsu Chemical) | 0.2 |
| 11. | Ethanol | 4.0 |
| 12. | Amodimethicone (SM8702C; product of Dow Corning) | 0.5 |
| 13. | Hydrolyzed keratin (Promois WK; product of Seiwa Kasei) | 0.5 |
| 14. | Purified water | balance |

(Method for Preparation)
A. Components 1–10 were heated, dissolved and mixed homogeneously.
B. Components 11–14 were mixed homogeneously.
C. B was added to A slowly, emulsified and homogenized, thus the hair set lotion was obtained.

The obtained hair set lotion was not so oily, has good penetration ability and light feel at actual use, further excellent in stability.

Example 34

W/O Emulsified Type Solid Foundation

| | (Components) | (%) |
|---|---|---|
| 1. | Isotridecyl isononanoate | 10.0 |
| 2. | Glyceryl trioctanoate | balance |
| 3. | Octamethylcyclotetrasiloxane | 10.0 |
| 4. | Dimetylpolysiloxane | 5.0 |
| 5. | Pentaerythritol rhodinate | 2.0 |
| 6. | Liquid paraffin | 10.0 |
| 7. | Ceresin wax | 4.0 |
| 8. | Inulin carboxylic acid ester (Synthesis Ex. 2) | 7.0 |
| 9. | Cetyl dimethicone copolyol (ABIL EM-90; product of Goldschmidt) | 2.0 |
| 10. | Silicone treated titanium dioxide | 6.0 |
| 11. | Silicone treated sericite | 3.0 |
| 12. | Silicone treated talc | 5.0 |
| 13. | Silicone treated red oxide of iron | 0.2 |
| 14. | Silicone treated yellow oxide of iron | 2.0 |
| 15. | Silicone treated black oxide of iron | 0.1 |
| 16. | Silicone treated spherical silica | 5.0 |
| 17. | 1,3-butylene glycol | 7.0 |
| 18. | Glycerin | 2.0 |
| 19. | Preservative | q.s. |
| 20. | Purified water | 10.0 |
| 21. | Perfume | q.s. |

(Method for Preparation)
A. Components 1–8 were mixed and dissolved homogeneously.
B. Components 9–16 were added to A and mixed homogeneously by a roll mill.
C. Components 17–21 were mixed homogeneously.
D. C was added to B and emulsified at 80° C.
E. Then filled into a dish at the temperature of 80° C. and cooled down.

Thus the W/O emulsified type solid foundation was obtained.

The obtained W/O emulsified type solid foundation had light feel and good adhesion at actual use, further was not sticky and was excellent in long lasting of makeup and stability.

Example 35

O/W Type Cream

| | (Components) | (%) |
|---|---|---|
| 1. | Acrylates/C-30 Alkyl Acrylate crosspolymer (CARBOPOL ® 1342; product of BF Goodrich) | 0.45 |
| 2. | Carbomer (CARBOPOL ® 940; product of BF Goodrich) | 0.45 |
| 3. | Purified water | balance |
| 4. | Glycerin | 1.0 |
| 5. | 1,3-butylene glycol | 16.0 |
| 6. | Methylparaben | q.s. |
| 7. | Polyoxyethylene(20)polyoxypropylene(8)cetylether | 0.5 |
| 8. | Triethanolamine | 0.9 |
| 9. | Inulin carboxylic acid ester (Synthetic Ex. 5) | 1.6 |
| 10. | Decamethylcyclopentasiloxane | 6.4 |
| 11. | Phenyl trimethicone | 0.5 |
| 12. | Acrylates/stearyl-acrylate/dimethicone acrylates copolymer (KP-561; product of Shin-Etsu Chemical) | 1.5 |
| 13. | N-phytostreryl/octyldodecyl lauroyl glutamate (ELDEW ® PS-203; product of Ajinomoto) | 1.0 |

(Method for Preparation)
A. Components 9–13 were heated and mixed homogeneously at 60° C.
B. Components 1–8 were mixed and dissolved homogeneously at 60° C.
C. A was added to B, stirred and emulsified.
D. C was cooled down, thus the O/W type cream was obtained.

The obtained O/W type cream had light feel and good adhesion at actual use, further is excellent in stability.

Examples 36–40 and Comparative Examples 8–12

O/W Type Emulsified Cream.

The creams component shown in Table 3 were prepared, and the state of emulsion, feeling at the actual use and stability were evaluated according to following method. The obtained evaluation results were also summarized in Table 3.

TABLE 3

| | | Example | | | | | Comparative Example | | | | (%) |
|---|---|---|---|---|---|---|---|---|---|---|---|
| | Content | 36 | 37 | 38 | 39 | 40 | 8 | 9 | 10 | 11 | 12 |
| 1 | Cethyl dimethicone copolyol (*1) | 1.5 | 1.5 | | | 0.5 | 1.5 | | | | 1.5 |
| 2 | Diglyceryl mono isostearate (HLB5.5) | | | 1.5 | 1.5 | 1 | | 1.5 | 1.5 | 1.5 | |
| 3 | Decamethylcyclopenta-siloxane | 15 | 10 | 5 | 5 | 10 | 15 | | 5 | 10 | 10 |

TABLE 3-continued (%)

|   | Content | Example | | | | | Comparative Example | | | | |
|---|---|---|---|---|---|---|---|---|---|---|---|
|   |   | 36 | 37 | 38 | 39 | 40 | 8 | 9 | 10 | 11 | 12 |
| 4 | Dimethylpolysiloxane (10 cs) | 1 | 1 | 1 | 1 | 1 | 1 |   | 1 | 1 | 1 |
| 5 | Cetyl isooctanoate | 5 | 3 | 7 | 7 | 5 | 5 | 5 | 7 | 5 | 5 |
| 6 | Liquid paraffin | 5 | 5 | 10 | 15 |   | 5 | 5 | 10 | 5 | 5 |
| 7 | Meadowfoam seed oil |   |   | 3 | 5 | 3 |   | 5 | 3 | 5 | 5 |
| 8 | Inulin carboxylic acid ester (synthesis Ex. 3) | 1 | 5 | 5 | 7 | 10 |   | 5 |   |   |   |
| 9 | Inulin carboxylic acid ester (synthesis Ex. 10) |   |   |   |   |   |   | 5 |   |   |   |
| 10 | Dextrin palmitate (*2) |   |   |   |   |   |   |   |   | 5 |   |
| 11 | Sucrose fatty acid ester (*3) |   |   |   |   |   |   |   |   |   | 5 |
| 12 | Perfume | 0.1 | 0.1 | 0.1 | 0.1 | 0.1 | 0.1 | 0.1 | 0.1 | 0.1 | 0.1 |
| 13 | Methylparaben | 0.2 | 0.2 | 0.2 | 0.2 | 0.2 | 0.2 | 0.2 | 0.2 | 0.2 | 0.2 |
| 14 | 1,3-butylene glycol | 12 | 12 | 12 | 12 | 12 | 12 | 12 | 12 | 12 | 12 |
| 15 | Purified water | 58.9 | 61.9 | 54.9 | 45.9 | 56.9 | 59.9 | 65.9 | 54.9 | 54.9 | 54.9 |
| 16 | Sodium chloride | 0.3 | 0.3 | 0.3 | 0.3 | 0.3 | 0.3 | 0.3 | 0.3 | 0.3 | 0.3 |
| Evaluation items |   |   |   |   |   |   |   |   |   |   |   |
| Emulsified state |   | ○ | ◎ | ◎ | ○ | ◎ | Δ | ○ | Δ | Δ | Δ |
| Feeing at the practical use |   |   |   |   |   |   |   |   |   |   |   |
| extension at coating |   | ○ | ◎ | ◎ | ○ | ○ | Δ | Δ | Δ | Δ | X |
| non sticking |   | ○ | ◎ | ◎ | ○ | ○ | Δ | X | Δ | Δ | X |
| Stability | at 45° C. | ◎ | ○ | ◎ | ○ | ◎ | Δ | ○ | Δ | Δ | X |
|   | at 5° C. | ◎ | ◎ | ◎ | ○ | ◎ | Δ | ○ | Δ | Δ | X |

Remarks:
(*1) ABIL EM-90 (product of Goldschmidt)
(*2) degree of substitution by acyl group 2.2: Rheopearl KL (product of Chiba Flour Milling)
(*3) sugar wax S-10E (product of Dai-ichi Kogyo Seiyaku)

(Method for preparation)
A. Components 1–12 were heated at 60° C. then mixed and dispersed.
B. Components 13–16 were heated at 60° C. then mixed and dispersed.
C. B was added to A slowly, emulsified, then cooled down and a cream was obtained.

(Method for Evaluation)
(1) Emulsion State
The prepared emulsion was observed by an optical microscope, and the uniformity of the emulsion particles were evaluated according to following judge standard.

[judgement]: [evaluation]
◎: excellently uniform
○: uniform
Δ: emulsion particles were slightly uneven
X: bonding of emulsion particles are coagulated (2) Feeling at the Actual Use
The specimen of Examples and Comparative Examples were test used by 20 women panellers, and extending and spreading feature and light feel at the actual use were evaluated according to following judge standard and the average score is indicated.

[Evaluation standard]
5: very good
4: good
3: normal
2: slightly bad
1: bad

[Judgement]
◎: average score is 4.5 or more
○: average score is 3.5 or more but less than 4.5
Δ: average score is 2.5 or more but less than 3.5
X: average score is less than 2.5

(3) Stability
Preserved in an incubator of 45° C. and 5° C. for one month and the change of the appearance is evaluated according to following judge standard.

[Judgement]
◎: not changed completely
○: not changed almost
Δ: slightly changed
X: obviously changed As clearly understood from the results of Table 3, the emulsion state of the specimen of cream of Examples 36–40 was good, had excellent extending feature, spreading feature and light feel at the actual use and had good stability.

Example 41

Beauty Lotion

|   | (Components) | (%) |
|---|---|---|
| 1. | PEG-3 Dimethicone (KF6015; product of Shin-Etsu Chemical) | 1.5 |
| 2. | Cetyl dimechicone copolyol (ABIL EM-90; product of Goldschmidt) | 1.0 |
| 3. | Sorbitan sesquiisostearate | 1.5 |
| 4. | Decamethylcyclopentasiloxane | 10.0 |
| 5. | Isononyl isomyristate | 8.0 |
| 6. | Perfluoropolyether (Fomblin HC/04; product of Ausimont) | 0.5 |
| 7. | Methylparaben | 0.2 |
| 8. | Perfume | 0.1 |
| 9. | Inulin carboxylic acid ester (Synthesis Ex. 2) | 0.7 |
| 10. | Inulin carboxylic acid ester (Synthesis Ex. 9) | 0.3 |
| 11. | Purified water | 59.7 |

-continued

| | (Components) | (%) |
|---|---|---|
| 12. | Glycerin | 3.0 |
| 13. | Propylene glycol | 10.0 |
| 14. | Magnesium ascorbate | 3.0 |
| 15. | Sodium citrate | 0.5 |

(Method for Preparation)

A. Components 1–10 were mixed and dispersed at 70° C.
B. Components 11–15 were mixed and dispersed at 70° C.
C. B was added slowly into A and emulsified, then cooled down, and a beauty lotion was obtained.

The obtained beauty lotion had excellent extending feature and spreading feature and good feel at the actual use. Further, the beauty lotion was stable after over than one month preservation at 45° C. and 5° C.

Example 42

Moisture Pack

| | (Components) | (%) |
|---|---|---|
| 1. | Cetyl dimethicone copolyol (ABIL EM-90; product of Goldschmidt) | 3.0 |
| 2. | Decamethylcyclopentasiloxane | 5.0 |
| 3. | Isotridecyl isononanoate | 15.0 |
| 4. | Liquid paraffin | 1.0 |
| 5. | Microcrystalline wax | 0.5 |
| 6. | Inulin carboxylic acid ester (Synthesis Ex. 4) | 1.0 |
| 7. | Methylpraben | 0.2 |
| 8. | Perfume | 0.1 |
| 9. | Silicone treated titanium dioxide | 5.0 |
| 10. | Silicone treated red oxide of iron | 0.2 |
| 11. | Nylon powder | 1.0 |
| 12. | Ethanol | 3.0 |
| 13. | Purified water | balance |
| 14. | Diglycerin | 3.0 |
| 15. | 1,3-butylene glycol | 15.0 |
| 16. | Sodium lactate | 1.0 |
| 17. | D & C Red No.6 | q.s. |

(Method for Preparation)

A. Components 1–11 were mixed and dispersed at 70° C.
B. Components 12–17 were mixed and dispersed at room temperature.
C. B was added slowly into A and emulsified, then cooled down, and a moisture retention pack composition was obtained.

The obtained moisture pack had excellent extending feature and spreading feature and good feel at the actual use. Further, the moisture pack was stable after over than one month preservation at 45° C. and 5° C.

Example 43

Cleansing Milk

| | (Components) | (%) |
|---|---|---|
| 1. | PEG-10 Dimethicone (KF6017; product of Shin-Etsu Chemical) | 1.5 |
| 2. | Diglyceril monoisostearate | 1.0 |
| 3. | Isononyl isononanoate | 10.0 |
| 4. | Octamethylcyclotetrasiloxane | 10.0 |
| 5. | Liquid paraffin | 5.0 |
| 6. | Phenyl trimechicone (&) dimethicone/phenyl vinyl dimethicone crosspolymer (KSG-18; product of Shin-Etsu Chemical) | 1.0 |
| 7. | Inulin carboxylic acid ester (Synthesis Ex. 5) | 1.0 |
| 8. | Methylparaben | 0.1 |
| 9. | Perfume | 0.1 |
| 10. | Ethanol | 15.0 |
| 11. | Purified water | 52.0 |
| 12. | Polyethyleneglycol | 3.0 |
| 13. | Sodium phosphate | 0.3 |

(Method for Preparation)

A. Components 1–9 were mixed and dispersed at 70° C.
B. Components 10–13 were mixed and dispersed at the room temperature.
C. B was added slowly into A and emulsified, then cooled down, and a cleansing milk was obtained.

The obtained cleansing milk had excellent extending feature and spreading feature and good feel at the actual use. Further, the cleansing milk was stable after over than one month preservation at 45° C. and 5° C.

Example 44

Sunscreening Composition

| | (Component) | (%) |
|---|---|---|
| 1. | PEG-10 Dimethicone (KF6017; product of Shin-Etsu Chemical) | 1.0 |
| 2. | Dimethylpolysiloxane | 5.0 |
| 3. | Octamethylcyclotetrasiloxane | 20.0 |
| 4. | Isotridecyl isononanoate | 5.0 |
| 5. | Octylmethoxy cinnamate | 5.0 |
| 6. | Inulin carboxylic acid ester (Synthesis Ex. 1) | 0.6 |
| 7. | Inulin carboxylic acid ester (Synthesis Ex. 8) | 0.4 |
| 8. | Methylparaben | 0.2 |
| 9. | Perfume | 0.2 |
| 10. | Silicone treated fine particle of titanium dioxide | 10.0 |
| 11. | Silicone treated fine particle of zinc oxide | 10.0 |
| 12. | Trimethylsiloxysilicate/decamethylcyclopenta siloxane (KP7312J; product of Shin-Etsu Chemical) | 0.5 |
| 13. | Ethanol | 10.0 |
| 14. | Purified water | balance |
| 15. | Dipropyleneglycol | 3.2 |
| 16. | Sodium chloride | 0.2 |

(Method for Preparation)

A. Components 1–12 were mixed and dispersed at 70° C.
B. Components 13–16 were mixed and dispersed at the room temperature.
C. B was added slowly into A and emulsified, then cooled down, and a sunscreening composition was obtained.

The obtained sunscreening composition displayed excellent extending and spreading at the applying and had good feel at the actual use, had good water resistance and had excellent sun screening effect. Further, the sunscreening composition was stable after over than one month preservation at 45° C. and 5° C.

Example 45
W/S (Water in Silicone) Type Cream

| | (Component) | (%) |
|---|---|---|
| 1. | Decamethylcyclopentasiloxane | 20.0 |
| 2. | Low viscosity methyl polysiloxane (KF-96A 6cs; product of Shin-Etsu Chemical) | 3.0 |
| 3. | Low viscosity methyl polysiloxane (KF-96A 2cs; product of Shin-Etsu Chemical) | 2.0 |
| 4. | Cetyl dimethicone copolyol (ABIL EM-90; product of Goldschmidt) | 1.0 |
| 5. | PEG-10 Dimethicone (KF6017; product of Shin-Etsu Chemical) | 1.5 |
| 6. | Inulin carboxylic acid ester (Synthesis Ex. 1) | 2.0 |
| 7. | Methylparaben | 0.2 |
| 8. | Perfume | 0.1 |
| 9. | Purified water | 58.2 |
| 10. | Glycerin | 1.0 |
| 11. | Sodium chloride | 1.0 |
| 12. | 1,8-butyleneglycol | 10.0 |

(Method for Preparation)
A. Components 1–8 were mixed and dispersed at 70° C.
B. Components 9–12 were mixed and dispersed at 70° C.
C. B was added to A slowly, stirred and emulsified, then cooled down and a cream was obtained.

The obtained cream displayed excellent extending and spreading at the applying and had good feel at the actual use. Further, the cream was stable after over than one month preservation at 45° C. and 5° C.

Example 46
W/S (Water in Silicone) Type Cream

| | (Components) | (%) |
|---|---|---|
| 1. | Decamethylcyclopentasiloxane | 20.0 |
| 2. | Isotridecyl isononanoate | 3.0 |
| 3. | Decamethyltetrasiloxane (KF-96A 1.5cs; product of Shin-Etsu Chemical) | 2.0 |
| 4. | Poly(PEG/PPG/butylene/dimethicone) copolymer (FZ-2222; product of Nippon Unicar) | 1.0 |
| 5. | PEG-9 polydimethylsiloxyethyldimethicone (KF 6028; product of Shin-Etsu Chemical) | 1.5 |
| 6. | Inulin carboxylic acid ester (Synthesis Ex. 1) | 1.0 |
| 7. | Aluminium dicetyl phosphate | 1.0 |
| 8. | Glyceryl behenate/eicosadioate (Nomcort HK-G; product of Nisshin Oil Mills) | 0.2 |
| 9. | Methylparaben | 0.2 |
| 10. | Perfume | 0.1 |
| 11. | Purified water | 58.0 |
| 12. | Ethanol | 1.0 |
| 13. | Sodium chloride | 1.0 |
| 14. | Dipropylene glycol | 10.0 |

(Method for Preparation)
A. Components 1–10 were mixed and dispersed at 70° C.
B. Components 11–14 were mixed and dispersed at 70° C.
C. B was added to A slowly, stirred and emulsified, then cooled down and a cream was obtained.

The obtained cream displayed excellent extending and spreading at the applying and had good feel at the actual use. Further, the cream was stable after over than one month preservation at 45° C. and 5° C.

Example 47
SUN CARE (T.M.) Milky Lotion

| | (Component) | (%) |
|---|---|---|
| 1. | PEG-9 polydimethylsiloxyethyl dimethicone (KF-6028; product of Shin-Etsu Chemical) | 1.0 |
| 2. | Dimethicone/phenyl vinyl dimethicone crosspolymer (KSG-8;. product of Shin-Etsu Chemical) | 1.0 |
| 3. | Octamethylcyclotetrasiloxane | 11.0 |
| 4. | Isotridecyl isononaoate | 1.0 |
| 5. | Inulin carboxylic acid ester (Synthesis Ex. 3) | 0.4 |
| 6. | Inulin carboxylic acid ester (Synthesis Ex. 9) | 0.6 |
| 7. | Octylmethoxycinnamate | 3.0 |
| 8. | Methylparaben | 0.1 |
| 9. | Perfume | 0.1 |
| 10. | Trimethylsiloxysilicate/decamethylcyclopentasiloxane (KF7312J; product of Shin-Etsu Chemical) | 0.5 |
| 11. | Ethanol | 10.0 |
| 12. | Purified water | 66.3 |
| 13. | Dipropylene glycol | 3.0 |
| 14. | Sodium chloride | 2.0 |

(Method for Preparation)
A. Components 1–10 were mixed and dispersed at 70° C.
B. Components 11–14 were mixed and dispersed at 70° C.
C. B was added to A slowly, stirred and emulsified, then cooled down and SUN CARE (T.M.) milky lotion was obtained.

The obtained SUN CARE (T.M.) milky lotion has light feel and good adhesion at actual use. Further, was excellent at long term preservative stability and fluidity.

What is claimed is:

1. A cosmetic composition comprising, component (A) and component (B), wherein, (A) is carboxylic acid ester of inulin and/or hydrolyzed inulin whose degree of substitution by acyl group is larger than 1, and (B) is cyclic silicone oil.

2. The cosmetic composition of claim 1 is the oily cosmetic composition further containing oleophilic component.

3. The cosmetic composition of claim 1 is the W/O emulsified cosmetic composition which further contains aqueous component and an emulsifier.

4. The cosmetic composition according to any one of claims 1 to 3, wherein acyl group which composes component (A) is an acyl group of carbon number 14 to 22.

5. The cosmetic composition according to any one of claims 1 to 3, wherein a part or all of acyl group which composes component (A) is palmitoyl group and/or stearoyl group.

6. The cosmetic composition according to any one of claims 1 to 3 is further containing dextrin carboxylic acid ester whose degree of substitution by acyl group is from 1.5 to 2.5.

7. The cosmetic composition according to any one of claims 1 to 3 wherein the acyl group composing of component (A) is acyl group of carbon number 14 to 22 and further containing dextrin carboxylic acid ester whose degree of substitution by acyl group is 1.5 to 2.5.

8. The cosmetic composition according to any one of claims 1 to 3 wherein a part or all of acyl group composing of component (A) is palmitoyl group and/or stearoyl group and further containing dextrin carboxylic acid ester whose degree of substitution by acyl group is 1.5 to 2.5.

9. The cosmetic composition according to any one of claims 1 to 3, wherein cyclic silicone oil of component (B) is at least one selected from the group consisting of octamethylcyclotetrasiloxane, decamethylcyclopentasiloxane and dodecamethylcyclohexasiloxane.

10. An oily cosmetic composition comprising, component (A-1), component (B) and component (C); wherein, (A-1) is 5–20 wt. % of a gelling agent containing more than 50 wt. % of (a) carboxylic acid ester of inulin and/or hydrolyzed inulin whose degree of substitution by acyl group is larger than 1 and (b) dextrin carboxylic acid whose degree of substitution by acyl group is 1.5 to 2.5 to the total weight, (B) is 30–90 wt. % of at least one cyclic silicone oil selected from the group consisting of octamethylcyclotetrasiloxane, decamethylcyclopentasiloxane and dodecamethylcyclohexasiloxane and (C) is 0.1–40 wt. % of powder.

11. The oily cosmetic composition of claim 10, wherein component (A-1) contains more than 50 wt. % of (a) carboxylic acid ester of inulin and/or hydrolyzed inulin whose degree of substitution by acyl group is larger than 1 and (b) dextrin carboxylic acid whose degree of substitution by acyl group is 1.5 to 2.5 to the total weight, wherein the blending weight ratio of (a) and (b) is (b)/(a)=0.5–2.

12. The oily cosmetic composition of claim 10 or claim 11, wherein a part or all of carboxylic acid which composes component (A) is palmitoyl group and/or stearoyl group.

13. (Currently amended) A W/O emulsified cosmetic composition comprising, component (A-1), component (B), component (D) and component (E);

wherein (A-1) is 1–20 wt. % of a gelling agent containing more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 2.5 to the total weight, (B) is 10–90 wt. % of at least one cyclic silicone oil selected from the group consisting of octamethylcyclotetrasiloxane, decamethylcyclopentasiloxane, and dodecamethylcyclohexasiloxane, (D) is 0.1 to 10 wt. % of an emulsifier and (E) is 1–80 wt. % of aqueous component.

14. The W/O emulsified cosmetic composition of claim 13, wherein component (A-1) contains more than 50 wt. % of (a) carboxylic acid ester of inulin and/or hydrolyzed inulin whose degree of substitution by acyl group is larger than 1 and (b) dextrin carboxylic acid ester whose degree of substitution by acyl group is 1.5 to 2.5 to the total weight, wherein the blending ratio of (a) and (b) is (b)/(a)=0.5–2.

15. The W/O emulsified cosmetic composition of claim 13 or claim 14, wherein a part or all of acyl group which composes component (A) is palmitoyl group and/or stearoyl group.

* * * * *